US000001440H

United States Statutory Invention Registration [19]

[11] Reg. Number: H1440

New et al.

[43] Published: May 2, 1995

[54] FITTED BELT FOR ABSORBENT GARMENT

[76] Inventors: Nancy A. New; Gary D. LaVon; David R. Bennett, all of 6100 Center Hill Rd., Cincinnati, Ohio 45224

[21] Appl. No.: 44,562

[22] Filed: Apr. 7, 1993

Related U.S. Application Data

[60] Division of Ser. No. 814,302, Dec. 20, 1991, abandoned, which is a continuation of Ser. No. 707,234, May 21, 1991, abandoned, which is a continuation of Ser. No. 454,104, Dec. 20, 1989, abandoned.

[51] Int. Cl.[6] ..... A61F 13/16

[52] U.S. Cl. ..... 604/386; 604/385.1; 604/402

[58] Field of Search ..... 604/383, 386, 387, 392–396, 604/401, 402, 345, 397–400, 385.1–385.2; 128/96.1, 98.1, 100.1, 152; 2/311, 312

[56] References Cited

U.S. PATENT DOCUMENTS

| | | | |
|---|---|---|---|
| 415,475 | 11/1889 | Steinmetz | 604/398 |
| 631,629 | 8/1899 | Ferris | 604/386 |
| 813,176 | 2/1906 | Schick | 604/402 |
| 849,725 | 4/1907 | Cook | 604/398 |
| 880,928 | 3/1908 | Slater | 604/402 |
| 1,328,406 | 1/1920 | Van Alstyn | 604/402 |
| 1,676,288 | 7/1928 | Schlosser | 604/402 |
| 1,683,125 | 9/1928 | Brady et al. | 604/402 |
| 1,761,222 | 6/1930 | McCullough | 604/402 |
| 2,011,027 | 8/1935 | Ballard et al. | 128/289 |
| 2,097,903 | 11/1937 | Wallis | 604/394 |
| 2,141,105 | 12/1938 | Eller et al. | 604/394 |

(List continued on next page.)

FOREIGN PATENT DOCUMENTS

| | | | |
|---|---|---|---|
| 425638 | 6/1911 | France | 604/401 |
| 2566631A | 1/1986 | France . | |
| 2586558 | 3/1987 | France . | |
| 2606257 | 5/1988 | France . | |
| 0010097 | 12/1902 | Germany | 604/401 |
| 431947 | 7/1926 | Germany | 604/397 |
| 3526499 | 11/1986 | Germany | 2/311 |
| 0004217 | 9/1891 | Switzerland | 604/402 |
| 0010119 | of 1894 | United Kingdom | 604/392 |
| 0409056 | 4/1934 | United Kingdom | 604/401 |
| 779161 | 7/1957 | United Kingdom | 604/401 |

*Primary Examiner*—David Brown

[57] ABSTRACT

Disclosed is a disposable absorbent garment having a belt. The belt may either be integral with or detachable from the absorbent portion of the garment. The belt is arcuate so that one laterally extending edge of the belt is longer than the other laterally extending edge of the belt. This arrangement provides a better fitting belt which more discretely conforms to the contours of the wearer and is less noticeable under clothing.

Alternatively, the belt may have a portion which is worn relatively high on the wearer's back, extends diagonally downward to the front of the wearer and is worn relatively low, below the stomach of the wearer in front. This arrangement provides a belt which generally does not interfere with the portions of the wearer's body which encounter large ranges of motion during normal movements of the body.

13 Claims, 7 Drawing Sheets

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

U.S. PATENT DOCUMENTS

| | | | |
|---|---|---|---|
| 3,407,813 | 10/1968 | Grippo et al. | 128/287 |
| 3,452,753 | 7/1969 | Sanford | 128/287 |
| 3,555,569 | 1/1971 | Jones | 2/311 |
| 3,603,316 | 9/1971 | Lehman | 2/312 |
| 3,618,608 | 11/1971 | Brink | 128/287 |
| 3,890,973 | 6/1975 | Davis et al. | 128/286 |
| 3,978,860 | 9/1976 | Stima | 604/385.1 |
| 4,051,854 | 10/1977 | Aaron | 128/284 |
| 4,158,906 | 6/1979 | Watson | 24/83 |
| 4,230,113 | 10/1980 | Mehta | 128/287 |
| 4,315,508 | 2/1982 | Bolick | 128/289 |
| 4,472,839 | 9/1984 | Johansen | 2/338 |
| 4,505,707 | 3/1985 | Feeney | 604/393 |
| 4,516,975 | 5/1985 | Mitchell | 604/385.2 |
| 4,610,682 | 9/1986 | Kopp | 604/385.1 |
| 4,617,022 | 10/1986 | Pigneul et al. | 604/391 |
| 4,692,110 | 2/1987 | Dudek | 604/385.1 |
| 4,728,326 | 3/1988 | Gilles | 604/391 |
| 4,769,023 | 9/1988 | Goebel et al. | 604/385 |
| 4,795,452 | 1/1989 | Blaney et al. | 604/385.1 |
| 4,842,596 | 6/1989 | Kielpikowski et al. | 604/385.2 |
| 4,886,511 | 12/1989 | Korpman | 604/385.2 |
| 4,932,950 | 6/1990 | Johnson | 604/392 |
| 4,964,860 | 10/1990 | Gipson et al. | |

FITTED BELT FOR ABSORBENT GARMENT

This is a division of application Ser. No. 7,814,302, filed on Dec. 20, 1991, (now abandoned) which was a continuation of application Ser. No. 7,707,234, filed on May 21, 1991 (now abandoned), which was a continuation of application Ser. No. 7,454,104, filed on Dec. 20, 1989 (now abandoned).

FIELD OF THE INVENTION

This invention is directed to absorbent garments worn to assist in the collection of bodily discharges of incontinent persons and, more particularly, to garments which have components fitted to the wearer.

BACKGROUND OF THE INVENTION

Disposable absorbent garments are well known in the art. Such disposable absorbent articles typically have a belt for attaching the article about the waist of the wearer. For example, U.S. Pat. No. 3,618,608 issued Nov. 9, 1971 to Brink discloses a diaper having a rectangularly shaped belt for attachment about the waist of the wearer and, similarly, French Patent No. 2,586,558,issued Mar. 6, 1987 to Mitrani discloses a disposable nappy having a rectangularly shaped belt.

Attempts have been made to improve the functioning of the belt, including joining the belt of disposable absorbent articles to portion of the garment itself. For example, French Patent No. 2,566,631 issued Jan. 3, 1986 to Le Pellec et al. discloses a napkin having the belts attached to the longitudinal side margins of the napkin.

Other attempts respecting the belt have been made, such as providing garments having one or more belts which encircle the sides of the wearer, as illustrated in U.S. Pat. Nos. 849,725 issued Apr. 9, 1907 to Cook; 2,011,027 issued Aug. 13, 1985 to Ballard et al.; and 3,452,753 issued Jul. 1, 1969 to Stanford. These patents disclose garments having one or more belts which encircle each side of the wearer and are joined to a central segment worn under the wearer's crotch.

One shortcoming of the prior art is that such belts typically do not fit tightly or conform closely to the wearer. This arrangement causes a bulky appearance under clothing and makes the presence of the absorbent garment more noticeable to others.

One reason that the belt of the garments of the prior art are often easily noticed is that the belts do not accommodate the taper and shape of the wearer's body contours under static conditions. Particularly, a rectangular belt does not conform to the divergence of the hips. Furthermore, the belts of absorbent articles according to the prior art may be placed against the body of the wearer at locations of the wearer's body having relatively large degrees of motion as the wearer encounters every day movements under dynamic conditions. Finally, the belts of the prior art may not optimize wearing comfort due to improper fit.

Therefore, it is an object of this invention to provide a belt which more closely fits the wearer and is less noticeable under the wearer's clothing under static conditions. It is also an object of this invention to provide a belt which does not interface with portions of the wearer's body which have relatively large degrees of motion during typical body movement under dynamic conditions. Finally, it is an object of this invention to provide a belt for an absorbent garment, which belt enhances comfort while the absorbent garment is worn.

SUMMARY OF THE INVENTION

The invention comprises a belt for use with an absorbent garment. The belt has spaced apart laterally extending edges and a means for causing one of the laterally extending edges to have a length which is greater than that of the other laterally extending edge while the belt is encircled about the waist of the wearer. The belt has a means for fastening to a portion of the absorbent garment, such as a disposable assembly, so that the absorbent garment may be worn about the waist or lower torso of the wearer.

In one embodiment, at least a portion of the laterally extending edges of the belt are arcuate within the plane of the belt and concave in the same direction. In a second embodiment the belt has at least one elastic segment which has differential extensibility in the lateral direction as measured across the width of the belt. In a third execution the belt has a central segment concave in a first direction within the plane of the belt, two intermediate segments outboard of, and juxtaposed with or adjacent the central segment, each intermediate segment having laterally extending edges arcuate within the plane of the belt and concave in a second direction generally opposite the first direction, and two distal segments, one juxtaposed with or adjacent each intermediate segment and being a generally rectilinear projection of the tangent of the distal end of the respective intermediate segment to which the distal segment is joined.

In one illustrative and nonlimiting execution the absorbent garment comprises a detachable belt which may be used with a plethora of disposable assemblies. In a second illustrative and nonlimiting execution the belt is joined, at a proximal end, to the backsheet of a disposable assembly. In a third illustrative and nonlimiting execution, the belt and disposable assembly are generally contiguous and do not have distinct, boundaries, yielding an integral structure.

BRIEF DESCRIPTION OF THE DRAWINGS

While the Specification concludes with claims particularly pointing out and distinctly claiming the present invention, it is believed that the invention will be better understood by the following description taken in conjunction with the accompanying drawings wherein like parts are given the same reference numeral, related or analogous parts are designated with a prime symbol and:

DETAILED DESCRIPTION OF THE INVENTION

Figure 1:
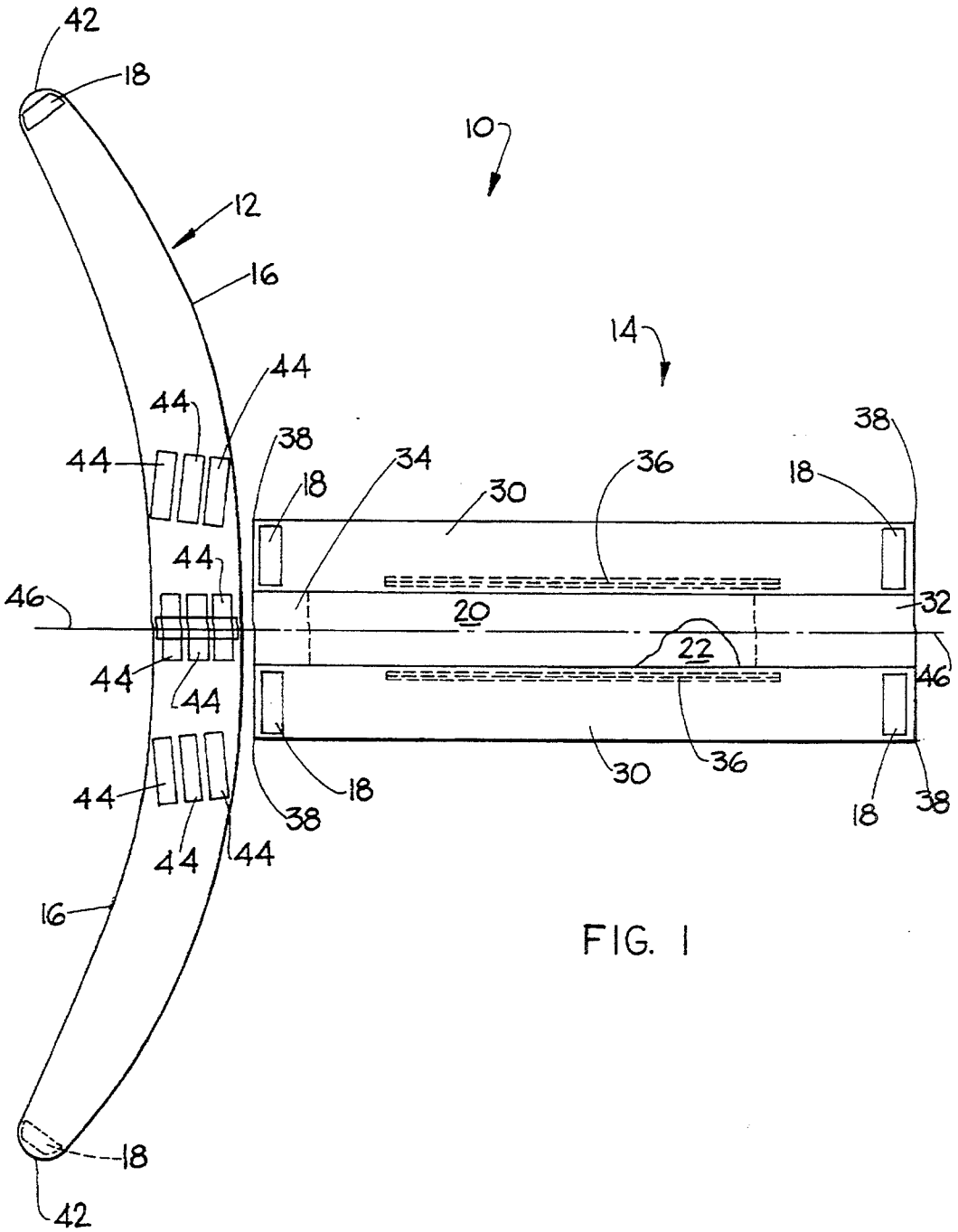
FIG. 1 is a top plan view of an absorbent article according to the present invention having no elastic induced contraction and showing the disposable assembly and belt separated.

As shown in FIG. 1, the invention comprises a detachable two piece absorbent garment 10, suitable for use as, but not limited to, an incontinence aid. The garment 10 features a belt 12 and a disposable assembly 14. The belt 12 may be made of receiving material bounded by two laterally extending edges 16. The receiving material is suitable for refastenably attaching desired portions of the belt 12 to complementary hook style mechanical fasteners.

The belt 12 further has a fastening means, preferably patches 18 of hook type material disposed on either end, for securing the belt 12 about the waist of a wearer. As used herein, components of a garment 10 are considered "detachable" if the components may be attached and removed more than one time, without destruction or undue distortion of either component.

The garment 10 herein described is laid out in the flat, uncontracted configuration of FIG. 1 unless otherwise specified. Examining each component of the garment 10 in more detail, the disposable assembly 14 is substantially symmetrically disposed about the longitudinal centerline 46 of the garment 10.

As used herein, the term "garment" refers to an article worn about the lower torso, typically by an incontinent person, for the collection of bodily discharges. The term "longitudinal" refers to an imaginary line, axis, or direction of the garment 10, which line, axis or direction extends between the transverse edges of the garment 10, is within the plane of the garment 10 as it is shown in the flat condition of FIG. 1, and is generally aligned with the vertical plane which bisects a standing wearer into left and right body halves. The term "lateral" refers to an imaginary line, axis or direction within the plane of the garment 10 as it is shown in the flat condition of FIG. 1, generally orthogonal the longitudinal direction and is generally sideways aligned relative the wearer.

The garment 10 described herein is sized to a wearer having a measurement ranging from about 81 centimeters to about 117 centimeters around the hips. It is to be understood by one skilled in the art that the garment 10 described herein is to be appropriately scaled for a differently sized wearer.

THE DISPOSABLE ASSEMBLY

The term "disposable assembly" refers to the combination of a backsheet 24, absorbent core 22, topsheet 20, and, if desired, one or more flaps 30 typically, but not necessarily, longitudinally coextensive of the topsheet 20 and backsheet 24. The disposable assembly 14 may be of any shape suitable for holding an absorbent core 22 about the anus and genitalia of the wearer. The term "disposable" refers to a garment 10, or component thereof, intended to be discarded after a single use and not to be laundered or otherwise restored and reused.

The disposable assembly 14 comprises a liquid pervious topsheet 20 which overlays an absorbent core 22 which, in turn, is intermediate and overlays a liquid impervious backsheet 24. The topsheet 20 and backsheet 24 are at least partially peripherally joined in face to face relation, circumscribing the periphery of the core 22 and capturing it in the desired intermediate position and orientation. Preferably, the topsheet 20 and backsheet 24 are joined throughout any portions which extend beyond, i.e., are outboard of, the periphery of the core 22. More preferably, the topsheet 20 and backsheet 24 are generally coextensive.

Figure 3:
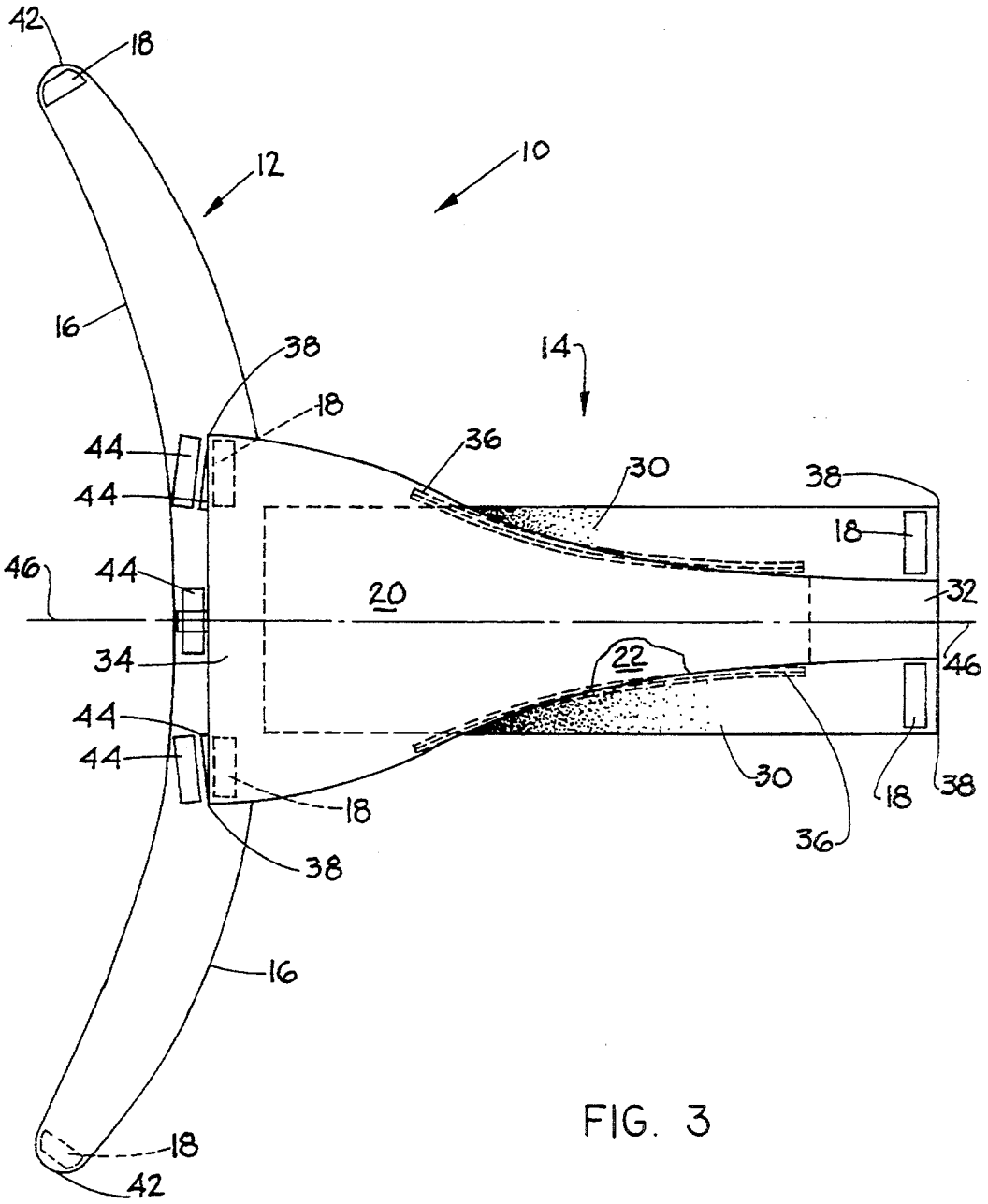
FIG. 3 is a top plan view of the article shown in FIG. 1 showing the inflected flaps of the disposable assembly attached to the belt.

The backsheet 24 and topsheet 20 have longitudinal side margins, as shown in FIG. 3, which are folded over the core 22 and topsheet 20, forming flaps 30 and define a somewhat C-shaped cross section. The flaps 30 may be elasticized to seal the disposable assembly 14 more closely to the legs of the wearer. The disposable assembly 14 may be generally rectangularly shaped, having front and rear waist margins 32 and 34 connected by longitudinal side margins, as seen in the top plan view, and which define four corners 38 of the flaps 30. A patch 18 of hook type mechanical fastening material is disposed at each corner 38 of the flaps 30 and faces away from the core 22.

The disposable assembly 14 may be of a quadrilateral shape, preferably rectangular, so that each half is substantially symmetric about the longitudinal centerline 46 and a mirror image of the other side. Preferably, the disposable assembly 14 has a greater longitudinal dimension than lateral dimension, to provide full coverage from the front waist margin 32 to the rear waist margin 34 around the lower abdominal region and torso of the wearer. For the embodiment described herein, a generally rectangular disposable assembly 14 having a longitudinal dimension of about 64 centimeters to about 79 centimeters preferably about 71 centimeters, and a lateral dimension of about 38 centimeters has been found suitable.

The disposable assembly 14 should be soft, flexible and provide comfort to the wearer. The term "flexible" refers to the condition of materials which are generally compliant and readily conform to the shape and contours of the human body. Preferably, the disposable assembly 14 is not noisy, to provide discretion for the wearer. Generally, the disposable assembly 14 should have minimal elongation in the longitudinal direction, so the garment 10 will be tight fitting in the crotch region and firmly position the absorbent core 22 against the body.

The disposable assembly 14 has two waist margins, a front waist margin 32 and a rear waist margin 34, both longitudinally outboard of the core 22. The front waist margin 32 and rear waist margin 34 are to the front and rear of the wearer, respectively, as the garment 10 is worn. The term "waist margin" refers to either of the two portions of the absorbent garment 10 which includes and is intermediate the lateral edge of the garment 10 and the corresponding lateral edge of the core 22 and is generally at the highest elevation of the disposable assembly 14 while the garment 10 is worn. Edges are "corresponding" if they are the closer of the two edges of like kind and disposed on the same side of the longitudinal or lateral centerline. If desired, the waist margins may be laterally extensible.

The disposable assembly 14 also has two longitudinal side margins, one disposed to either side of the longitudinal centerline 46 and towards the wearer's left and right sides. The term "longitudinal side margin" refers to that portion of the garment 10 intermediate the longitudinal edge of the garment 10 and the corresponding longitudinal edge of the core 22. The longitudinal side margins form the flaps 30 of the garment 10 as described in more detail below. Preferably, the longitudinal side margins and waist margins are formed from the coextensive portions of the topsheet 20 and backsheet 24 joined in face to face relation, which portions are respectively laterally and longitudinally outboard of the core 22.

To provide flaps 30 of a suitable geometry, the backsheet 24 and topsheet 20 are coextensive and wider, i.e., greater in lateral dimension, than the core 22. Each flap 30 should laterally extend about 5 to about 8 centimeters from the corresponding longitudinal edge of the core 22, so that the flap 30 can stand away from the core 22 and provide for containment of bodily discharges, particularly in the crotch region of the garment 10.

The core 22 is centered on and intermediate the topsheet 20 and backsheet 24, so that each longitudinal side margin may be folded about the longitudinal edge of the core 22, forming a flap 30. The term "flap" refers to the component of the garment 10, specifically of the disposable assembly 14, which overlays the core 22 and the outwardly facing surface of the topsheet 20. The proximal edge of the flap 30 is coincident with the fold line and is the longitudinal edge of the topsheet 20 and backsheet 24 at the peripheral seal adjacent the longitudinal edge of the core 22. When the flaps 30 are folded about this fold line, the distal edge of the flap 30 will overlay the longitudinal edge of the core 22 about 7 centimeters, providing a minimum distance of about 3.3 centimeters between the distal edge of the flap 30 and the longitudinal centerline 46.

This arrangement creates a urine target zone in the exposed area of the topsheet 20 between the flaps 30. The urine target zone is intermediate the flaps 30 and extends from about 5 centimeters to about 25 centimeters from the front lateral edge of the core 22 towards the rear waist margin 34. Al so the longitudinal dimension of the front waist margin 32 should not be too great, otherwise, a pocket too small for the male wearer may result. The target zone should be somewhat less than described above if the inflected flap 30 arrangement of FIG. 3 is not used.

When the flaps 30 overlay the topsheet 20 and core 22, the proximal edges of the flaps 30 are generally mutually parallel. The proximal edges of the flaps 30 and the longitudinal edges of the disposable assembly 14 intersect to define four corners, each corner having a patch 18 of hook type material complementary to the receiving material of the belt 12.

Disposed on at least one and preferably each of the four corners 38 and facing away from the topsheet 20, is an outwardly facing patch 18 of the hook type material, complementary to the receiving material of the belt 12. Thus, a pair of patches 18 of hook type material i s disposed at both the front and rear waist margins 32 and 34, with each patch 18 facing in the same general outward direction (away from the core 22). The patches 18 should preferably be juxtaposed with the corners and may laterally extend substantially the entire lateral dimension of the flaps 30.

Each patch 18 may be spaced inwardly from the lateral and longitudinal edges of the flaps 30 at least approximately 0.6 centimeters, to provide for variations in positioning during manufacture and obviate the rough edge of the patch 18 from contacting and irritating the ski n of the wearer. The patches 18 may be polygonol, preferably rectangular in shape. Such shape preferably has a greater longitudinal dimension than lateral dimension, with the longitudinal dimension being less than the width of the belt 12, to provide for longitudinal adjustment of the disposable assembly 14 relative to the belt 12.

The patches 18 may be joined to the flaps 30 using any means well known in the art, the joining strength of which means exceeds the desired peel and shear strengths. Hot melt adhesive bonding, as discussed above, using Minnesota Mining and Manufacturing Company model number XP0-9-035 adhesive has been found suitable. Patches 18 made of Minnesota Mining and Manufacturing Company Model No. XPO-0040 hook type material, described above, are particularly suitable and complementary to the receiving material of the belt 12 described herein.

The distal edges of the flaps 30 may monotonically taper towards the longitudinal centerline 46 as either waist margin 32 or 34, particularly the front waist margin 32, is approached. Alternatively the distal edges of the flaps 30 may be arcuate, particularly concave towards the longitudinal centerline 46, so that a wider access to the topsheet 20 is provided as the lateral centerline of the garment 10 is approached.

The distal edges of the flaps 30 may be reinforced, entirely or in part, with elastic 36 to form a barrier leg cuff which more securely seals the flaps 30 against the inner thigh of the wearer and provides a mechanism for the flaps 30 to be spaced from the core 22 and topsheet 20. The elastic 36 need not extend into the rear waist margin 34 of the garment 10. Further, the elastic 36 should not be disposed too close to any of the patches 18 of hook type material, particularly those patches 18 disposed near the front waist margin 32 of the garment 10, otherwise bunching and wrinkling of the garment 10 near the patches 18 may occur and the target zone for urine may be reduced, possibly allowing leakage, particularly for a male wearer.

Preferably, the elastic 36 is somewhat centered on the distal edge of the flap 30. The elastic 36 is preferably extended about 75 to about 95 percent, more preferably about 85 percent as the flaps 30 conform to the shape of the wearer. For the embodiment described herein, having a longitudinal dimension at the distal edges of the flaps 30 of about 71 centimeters, the elastic 36 may terminate at least about 3 to about 15 centimeters from the front waist margin 32 and about 3 to 25 centimeters from the rear waist margin 34.

The elastic 36 should provide a high degree of extensibility, without undue contractive force and should be under tension when joined to the garment 10. Elastic 42 which relaxes about 20 percent of its extended length when an applied load of about 400 grams is reduced to an applied load of about 100 grams force is adequate.

The elastic 36 may be either a single strand of elastomeric material, or parallel multiple strands of elastic 36 material, as desired. If a single strand of elastic 36 is selected, a rubber strand made by Fulflex Inc. of Middletown, Rhode Island and sold as Model No. 9411 has been found suitable. The single strand of elastic 36 may be adhered to the flap 30 with 691-336-20 adhesive sold by the Findley Adhesives Company of Wauwatosa, Wisconsin. This elastic 36 may be prestretched about 180 percent before being joined to the flap 30.

If multiple strands of elastic 36 are selected, 940 Decitex Lycra sold by the DuPont Corporation of Wilmington, Delaware and intermittently adhered to the flap 30 with a spiral adhesive pattern using the Findley H2031 works well. A particularly suitable execution has four parallel strands of the Lycra elastic 36, each prestretched about 250–450 percent, preferably about 300 percent, when joined to the flaps 30.

The elastic 36 is preferably joined to the flaps 30 intermediate the topsheet 20 and backsheet 24, so that the elastic 36 does not contact and irritate the skin of the wearer when the flaps 30 inflected or are folded about the longitudinal edges of the core 22. The elastic 36 may be attached to the flaps 30 using any method known in the art, such as that disclosed in U.S. Pat. No. 4,081,301, issued Mar. 28, 1978, to Buell, which patent is incorporated herein by reference for the purpose of showing a particularly preferred method of joining the elastic 36 to the flaps 30. Alternatively, the elastic 36 may be adhesively coated with an intermittent spiral pattern of adhesive.

The absorbent core 22 provides the means to collect and contain bodily discharges, particularly urine, deposited thereon. The term "core" refers to the component of the garment 10 which receives and retains the bodily discharges. The core 22 is disposable and should be conformable and nonirritating to the skin. Suitable core 22 materials include layers of tissue, such as cellulose wadding and fibrated communition pulp or airfelt, and absorbent gelling materials. The core 22 need not have a total absorbent capacity much greater than the total amount of bodily discharges to be absorbed and is preferably narrow and thin so as to be comfortable to the wearer. For the execution and wearer described herein, the capacity is preferably not less than about 350 grams of urine.

The core 22 should be sized to register with the disposable assembly 14 of the garment 10, and be laterally narrower than the topsheet 20 and backsheet 24. For the execution described herein, a generally quadrilaterally shaped core 22 having a greater longitudinal dimension than lateral dimension is suitable. Preferably, the core 22 is somewhat hourglass shaped, having notches to accommodate the legs. The core 22 may be about 56 centimeters in the longitudinal dimension, about 15 centimeters in lateral dimension at the notches, and about 23 centimeters in lateral dimension at the inboard lateral edges of the waist margins 32 and 34. This geometry provides a margin between the lateral edges of the core 22 and the corresponding lateral edge of the disposable assembly 14 of about 7.5 centimeters in longitudinal dimension.

The core 22 is preferentially interposed between the topsheet 20 and the backsheet 24 to prevent the absorbent material of the core 22 from shredding and becoming detached while the garment 10 is worn and to insure containment of bodily discharges. This arrangement also provides for a unitary disposable assembly 14 which can be easily attached to and detached from the belt 12.

The core 22 is preferentially joined to the backsheet 24. The term "join" refers to the condition where a first member or component is affixed, or connected, to a second member or component either directly; or indirectly, where the first member or component is affixed, or connected, to an intermediate member or component which in turn is affixed, or connected, to the second member or component. The association between the first member, or component, and the second member, or component, is intended to remain for the life of the garment 10. Joining is preferentially accomplished by adhesive bonding the core 22 to the backsheet 24. The adhesive may be applied in any suitable spray pattern or longitudinally oriented beads. Adhesive sold under the tradename 990C by the Findley Adhesives Company of Wauwatosa, Wisconsin, has been found to work well for this purpose.

The topsheet 20 is oriented towards and contacts the body of the wearer. The topsheet 20 is liquid pervious and should be flexible, clean in appearance, and somewhat opaque to hide bodily discharges collected in and absorbed by the core 22. The topsheet 20 should exhibit good strikethrough and rewet characteristics, permitting bodily discharges to rapidly penetrate the topsheet 20 to the core 22, but not flow back through the topsheet 20 to the skin of the wearer. A perforated polyolefinic film or nonwoven topsheet 20 having about 5 to about 60 percent open area, typically about 25% open area, and a thickness of about 0.01 to about 0.05 millimeters is suitable. Model P1522 film made by the Tredegar Film Products of Terre Haute, Indiana and James River Corporation of Richmond, Virginia Model Number MSP-T090 Celestra IV-0.55 nonwoven material have been found to work well.

The backsheet 24 may be any flexible, liquid impervious film, such as a polyolefinic film and prevents discharges absorbed by the core 22 from soiling the clothing and bedding of the wearer. The backsheet 24 may also be impervious to malodorous gases generated by absorbed bodily discharges, so that the malodors do not escape and become noticed by the wearer. A low density polyethylene backsheet 24 about 0.01 to about 0.05 millimeters in thickness preferably about 0.04 millimeters has been found to work well. Polyethylene films sold by the Tredegar Film Products as Model Number XP-3985 has been found particularly well-suited for this purpose.

In a variant embodiment (not shown), the outwardly facing patches 18 are not disposed on the flaps 30, but rather are joined to the exposed and outwardly facing surface of the backsheet 24. The disposable assembly 14 of the garment 10 may be thought of as having a lateral centerline bisecting the garment 10 into a front portion and a rear portion, to the front and rear of the wearer, as the garment 10 is worn, respectively. The disposable assembly 14 may be further thought of as having four quadrants, defined by the longitudinal centerline 46 and the lateral centerline.

In such an embodiment one patch 18 is disposed within each quadrant of the backsheet 24 defined by the longitudinal centerline 46 and lateral centerline. Preferably, each such patch 18 is juxtaposed with a corner 38 of the disposable assembly 14. Utilizing this arrangement, the patches 18 are attached to the inwardly facing surface of the belt 12 at both the front waist margin 32 and the rear waist margin 34.

If it is desired to join the patches 18 to both outwardly facing surfaces of the belt 12, the rear waist margin 34 may be outwardly folded about a laterally oriented line approximately 2.5 centimeters from such waist margin 32 and joined to the topsheet 20. If such an arrangement is selected, the disposable assembly 14 should be lengthened accordingly.

In another variant (not shown), a longitudinally oriented patch 18, disposed on the backsheet 24, at or near the longitudinal centerline 46, extends from the front portion of the garment 10 to the rear portion of the garment 10. Alternatively, two longitudinally oriented patches 18 may be provided on the backsheet 24, one patch 18 disposed on either side of the longitudinal centerline 46, each patch 18 preferably within the longitudinal marginal portions 32. Each longitudinally extending patch 18 extends into both the front and rear portions of the garment, preferably to the front and rear waist margins 32 and 34.

In a related variant (not shown), one longitudinally oriented outwardly facing patch 18, is disposed on each flap 30. The longitudinally oriented patch 18 extends from the front portion of the garment 10 to the rear portion of the garment 10, so that both the front and rear waist margins 32 and 34 may be secured to the belt 12.

In another variant (not shown) two laterally oriented patches 18 are joined to the backsheet 24. In such an embodiment, one patch 18, in the front portion and one patch 18 in the rear portion laterally extend to both sides of the longitudinal centerline 46, so that both the front and rear waist margins 32 and 34 may be attached to the belt 12. Additionally a patch 18 may be disposed on the backsheet 24 coincident with the longitudinal centerline 46.

It will be apparent to one skilled in the art that any of the aforementioned variants having an arrangement of patches 18 joined to the backsheet 24 will not have the inflected flaps 30 of FIG. 3 and may even omit such flaps 30.

Yet another variation is to substitute patches of adhesive 62 for the patches 18 of hook type material in any of the aforementioned executions. Suitable adhesive is sold by Eastman Chemical Products Company of Kingsport, Tennessee under the tradename Eastobond A-3. If adhesive patches 18 are selected, the belt 12 should be adapted to provide a complementary surface to which the patches 18 of the adhesive will readily adhere. A belt 12 having complementary zones corresponding to the positions of attachment of the patches 18 and made of polyethylene, in accordance with the aforementioned and incorporated U.S. Pat. No. 4,662,875 is suitable. Alternatively, the patches of adhesive 62 may be disposed on the belt 12 and the complementary zones disposed on the flaps 30 or backsheet 24 as described above.

THE BELT

The "belt" is the component of the garment 10 to which both waist margins 32 and 34 of the disposable assembly 14 are attached which encircles the waist of the wearer, and holds the disposable assembly 14 against the wearer. The belt 12 is bounded by two spaced apart laterally extending edges 16 which define the width of the belt 12. The belt 12 preferably has a width of about 6.5 centimeters to about 13 centimeters, preferably about 8 centimeters between the laterally extending edges 16, to provide for variations in longitudinal positioning of the disposable assembly 14. If the belt 12 is narrower, it may twist during application to the disposable assembly 14. If the belt 12 is wider, it may wrinkle and redmark the skin and interfere with the leg movements of the wearer.

The belt 12 further comprises a means for causing one laterally extending edge 16 to have a length greater than that of the other laterally extending edge 16 when the belt 12 is encircled about a wearer. Such means for causing a difference in length of the edges 16 results in fitting of the belt 12 to the shape of the wearer, and is not due to a mere difference in lengths of the edges 16 at the overlap of various portions of the belt 12. The belt 12 is, as shown in FIG. 1, generally arcuate in shape and has a curvilinear length taken generally midway between the laterally extending edges 16 of about 102 to about 117 centimeters, preferably about 112 centimeters between the two opposed distal ends 42, to accommodate the aforementioned range of wearer sizes.

The belt 12 is preferably reusable, and is not intended to be soiled by the collection of bodily discharges or disposed of when the core 22 becomes loaded by such bodily discharges. As used herein, the term "reusable" refers to a garment 10, or component thereof, intended to be laundered and restored rather than to be discarded after a single use. The belt 12 should be clean in appearance, nonirritating to the skin of the wearer, and able to accommodate a wide range of wearer sizes. Although not required, it may be desirable to have one belt 12 matched to a given wearer over a period of time or, alternatively and particularly for institutional use, a belt 12 may be laundered, sanitized and interchanged among various wearers.

The belt 12 has receiving material, disposed at various positions along the length, to provide for attachment of the belt 12 about the waist of the wearer and of the disposable assembly 14 to the belt 12. Preferably, the receiving material is disposed on both faces of the belt 12, and along the entire length of the belt 12, to provide for more versatility in attachment of the disposable assembly 14. As used herein, the term "receiving material" refers to material having an exposed surface with tightly spaced openings complementary to hook type material, discussed below, and which openings are defined by one or more strands or fibers, or; alternatively, material capable of localized elastic deformations, so that the complementary hook type material may become entrapped and not withdrawn without interference. For the embodiment described herein, loop material having a pile depth of about 0.8 millimeters works well.

The belt 12 may be of either single or double thickness, depending upon whether the receiving material has one or two exposed faces complementary to the hook type material. The openings or localized elastic deformations allow for entry of the hook type material into the exposed surface of the receiving material, while the fibers, strands or nondeformed areas of the receiving material prevent withdrawal or release of the hook type material until either it is so desired by the user or the peel or shear strength is exceeded. Loop style receiving material sold by Guilford Mills, Incorporated of New York, New York as Model Number 19029 has been found to work well.

Preferably, a patch 18 of hook type material complementary to the receiving material is disposed near each end of the belt 12, to provide for securing of the belt 12 about the waist of the wearer. As used herein, the term "hook type material" refers to any material having a fastening system joined to and projecting from a substrate. The fastening system may have one or more mechanical engaging means which project, typically radially, from a shank which is joined to the substrate or may be adhesive. The engaging means is typically the portion of the hook type material which penetrates and is secured to the exposed surface of the complementary receiving material. Suitable hook type material is sold by the Minnesota Mining and Manufacturing Company of Minneapolis, Minnesota as Model Number XPO-0040 and by Velcro U.S.A., Inc. of Manchester, New Hampshire as Hook 88. Hook type material and receiving material are considered "complementary" if the openings between the strands or fibers are sized to allow at least one engaging means of the hook type material to penetrate into the exposed surface of the receiving material and to be engaged or intercepted thereby.

The patch 18 of hook type material described herein, preferably has a peel strength of at least about 300 grams but which does not exceed about 1,000 grams to provide for adequate attachment of the components discussed herein, but which is not so great as to provide undue resistance when it is desired to remove the garment 10 or inspect it for the accumulation of bodily discharges. A peel strength of about 500 grams is generally preferred. The patch 18 should have a minimum shear strength of about 1,000 grams. A patch 18 of hook type material at each end of the belt 12 about 1.9 centimeters wide and coterminous with the longer edges of the belt 12 is generally suitable.

The laterally extending edges 16 of the belt 12 may be sewn or reinforced with a material, such as rib knit material, to prevent the belt 12 from becoming frayed or the exposed surfaces of receiving material from separating (if the belt 12 is made of a double thickness). The sewing, or other reinforcement, should be generally smooth, nonirritating to the skin of the wearer, and not provide an undue increase in the thickness of the belt 12, otherwise the wearer may experience discomfort.

The belt 12 may be provided with indicia 44, such as targets or visual markings, so that the longitudinal centerline 46 of the belt 12 becomes apparent and may be matched to the longitudinal centerline 46 of the disposable assembly 14. The indicia 44 may be sized to the shape of the hook type patches 18 disposed on the corners 38 of the flaps 30, to indicate to the user an appropriate location for attaching such patches 18 to the belt 12. The indicia 44 may be longitudinally spaced, to assist in adjustment of the belt 12, relative to the disposable assembly 14, in the longitudinal direction. The indicia 44 may be sewn, printed or applied to the belt 12 in any permanent manner.

The indicia 44 allow the user to repeatedly attach the disposable assembly 14 to the belt 12 on an ephemeral basis, so that readjustment and refitting (particularly in the longitudinal direction) is minimized. It will be apparent to one skilled in the art, that the herein described belt 12, even with spaced indicia 44, allows for infinite adjustment of the disposable assembly 14 relative to the receiving material of the belt 12. For example, if a wearer's size does not correspond to the placement of the indicia 44, the disposable assembly 14 may be attached to the belt 12 at any position intermediate the indicia 44. Indicia 44 which allow adjustment in accordance with the teachings of U.S. Pat. No. 4,662,875 issued May 5, 1987 to Hirotsu et al., and incorporated herein by reference for the purpose of showing a preferred type of indicia 44 and materials, are suitable.

As illustrated in FIG. 1, the belt 12 is preferably generally arcuate in shape. The arc of the belt 12 is defined by the laterally extending edges 16. A "laterally extending edge" is the border of the belt 12 which has a principally laterally aligned dimension and is principally horizontal when the belt 12 is encircled about a standing wearer. The laterally extending edges 16 are spaced apart by the width of the belt 12. The belt 12 has a means for causing one of the laterally extending edges 16 to have a length greater than the length of the other laterally extending edge 16 when the belt 12 is encircled about the wearer. The spaced apart laterally extending edges 16 are both arcuate within the plane of the belt 12. As used herein components are said to be "within the plane of the belt 12" when the belt 12 is laid out in a flat, uncontracted disposition and such components are coplanar and coincident with the plane of the belt 12.

It will be apparent to one skilled in the art that a suitable means for causing one laterally extending edge 16 to have a length greater than that of the other laterally extending edge 16 is that one laterally extending edge 16, typically the laterally extending edge 16 of lower elevation when the belt 12 is encircled about a standing wearer, has a lesser radius of curvature or subtends a greater arc than the other laterally extending edge 16. Thus, the laterally extending edges 16 of the belt 12 may either be of different radii of curvature, or of equal and nonconcentric radii of curvature.

In a preferred embodiment, the radius of curvature of each laterally extending edge 16 increases as the distal ends 42 of the belt 12 are approximated. As used herein the "distal ends" of the belt 12 are the free ends of the belt 12 and are disposed furthest from the centerline 46 of the belt 12. The "centerline" of the belt 12 is the laterally centered and longitudinally oriented line of the belt 12, which line corresponds in position to the spinal cord of the wearer when the belt 12 is worn in the desired manner. Generally, the distal ends 42 of the belt 12 are substantially isomerically and oppositely disposed from the centerline 46, so that the belt 12 has two symmetrically opposite halves, each a mirror image of the other. As used herein the term "outboard" means in a direction away from the centerline 46 and towards a distal end 42. Conversely, as used herein the term "inboard" is the direction generally opposite of outboard and away from a distal end 42 and oriented in sense towards the centerline 46.

A preferred manner in which the radii of curvature may increase as a laterally extending edge 16 of the belt 12 is approached is to have nonconcentric and generally equal radii of curvature for each laterally extending edge 16. If nonconcentric and generally equal radii of curvature are selected for the laterally extending edges 16 of the belt 12, the radii of curvature of each laterally extending edge 16 near the centerline 46 of the belt 12 may range from about 25 centimeters to about 102 centimeters. At the distal ends 42 of the belt 12, a suitable radius of curvature is about 360 to about 153 centimeters for each laterally extending edge 16. A particularly preferred shape for the laterally extending edges 16 is approximately parabolic, according to the formula $Y=aX^2$, wherein:

Y is the deviation of the edge 16 from the elevation at the centerline 46;

X is the lateral distance from the centerline 46; and a is a dimensionless constant.

While it will be apparent that other shapes are feasible a parabolic shape is generally preferred, so that the radius of curvature increases according to a cubic function.

Referring to Table I, twelve belts 12 are presented in the columns. The radius of curvature of each laterally extending edge 16 is shown in the rows, from 5 centimeters outboard of the centerline 46 to the distal ends 42 which are about 56 centimeters from the centerline 46. The top row is the value of the constant a. The bottom row is the difference (diff.) in radius of curvature between the centerline 46 and distal end 42.

It can be seen that the belts 12 become more acceptable as the value of the constant a ranges from about 1/20 to about 1/80, and particularly from about 1/30 to about 1/60. As the value of the constant a increases above this range (to the left side of the Table), the lower edge 16 of the belt 12 may not properly conform to the central portion of the wearer's back. As the value of the constant a decreases below this range (to the right side of the Table), the upper edge 16 of the belt 12 may not properly conform to the wearer's hips, and to a lesser extent not properly conform to the wearer's back. Generally, the constant a determines that a difference in radius of curvature between the centerline 46 and the distal end 42 of about 70 and about 175 centimeters is generally suitable.

edge 16 of lower elevation should have a lesser radius of curvature. With this structure, the parameter which governs the fit and acceptability of the belt 12 is the magnitude of the differences between the largest and smallest radii of curvature of each edge 12, i.e. the difference of the differences. As the magnitude of the differences increases, the laterally extending edges 16 converge as the distal end 42 is approached and the belt 12 may be too short. If the length is adequate, this arrangement may provide an unacceptably narrow belt 12 width. Preferably the magnitude of the differences between the radii of curvature is less than about 65 centimeters and more preferably less than about 25 centimeters.

Such a belt 12 may be constructed according to the columns of Table I, using a different, preferably adjacent, column for each laterally extending edge of the belt 12, so long as the magnitude of the difference between the differences of the last row is less than about 40 centimeters. The first laterally extending edge 16, which is of higher elevation on a standing wearer should have a greater radius of curvature, and hence smaller value of the constant a, than the second laterally extending edge 16, which is of lower elevation on a standing wearer. Therefore, using Table I, the lower edge 16 should be a column disposed to the left of the column selected for the upper edge 16. Preferably both columns are within the "Acceptable" range of Table I. It will be apparent that as the columns converge in value, the preferred foregoing belt 12 having noncon-

TABLE I

| | RADIUS OF CURVATURE AS A FUNCTION OF LATERAL POSITION | | | | | | | | | | | |
|---|---|---|---|---|---|---|---|---|---|---|---|---|
| constant | a = 1/15 | a = 1/20 | a = 1/25 | a = 1/30 | a = 1/36 | a = 1/39 | a = 1/42 | a = 1/50 | a = 1/60 | a = 1/70 | a = 1/80 | a = 1/90 |
| LDFC[1] | Radii of Curvature | | | | | | | | | | | |
| 5 | 21 | 27 | 33 | 39 | 47 | 50 | 54 | 64 | 77 | 89 | 102 | 115 |
| 10 | 28 | 32 | 37 | 42 | 49 | 53 | 56 | 66 | 78 | 91 | 103 | 116 |
| 15 | 40 | 40 | 43 | 47 | 54 | 57 | 60 | 69 | 81 | 92 | 105 | 117 |
| 20 | 59 | 53 | 53 | 55 | 60 | 63 | 65 | 74 | 85 | 96 | 108 | 120 |
| 25 | 88 | 72 | 67 | 66 | 68 | 70 | 72 | 79 | 89 | 100 | 111 | 123 |
| 30 | 128 | 97 | 85 | 80 | 79 | 80 | 81 | 87 | 95 | 105 | 116 | 127 |
| 36 | 181 | 129 | 107 | 98 | 93 | 92 | 93 | 96 | 102 | 111 | 121 | 131 |
| 41 | 249 | 171 | 136 | 119 | 109 | 107 | 106 | 106 | 111 | 118 | 127 | 137 |
| 46 | 335 | 222 | 171 | 145 | 129 | 125 | 122 | 119 | 121 | 126 | 134 | 143 |
| 51 | 439 | 284 | 213 | 176 | 153 | 146 | 140 | 133 | 132 | 136 | 142 | 150 |
| 56 | 567 | 358 | 263 | 213 | 180 | 170 | 162 | 150 | 145 | 147 | 151 | 158 |
| diff. | 546 | 332 | 230 | 174 | 133 | 119 | 108 | 86 | 69 | 57 | 49 | 43 |
| MoD[2] | 214 | 102 | 56 | 41 | 14 | 11 | 22 | 17 | 12 | 8 | 6 | |
| | unacceptable | marginally acceptable | | | | acceptable | | | | marginally acceptable | | unacceptable |

[1]Lateral Distance From Centerline
[2]Magnitude of Differences
(All dimensions in centimeters)

Figure 2:
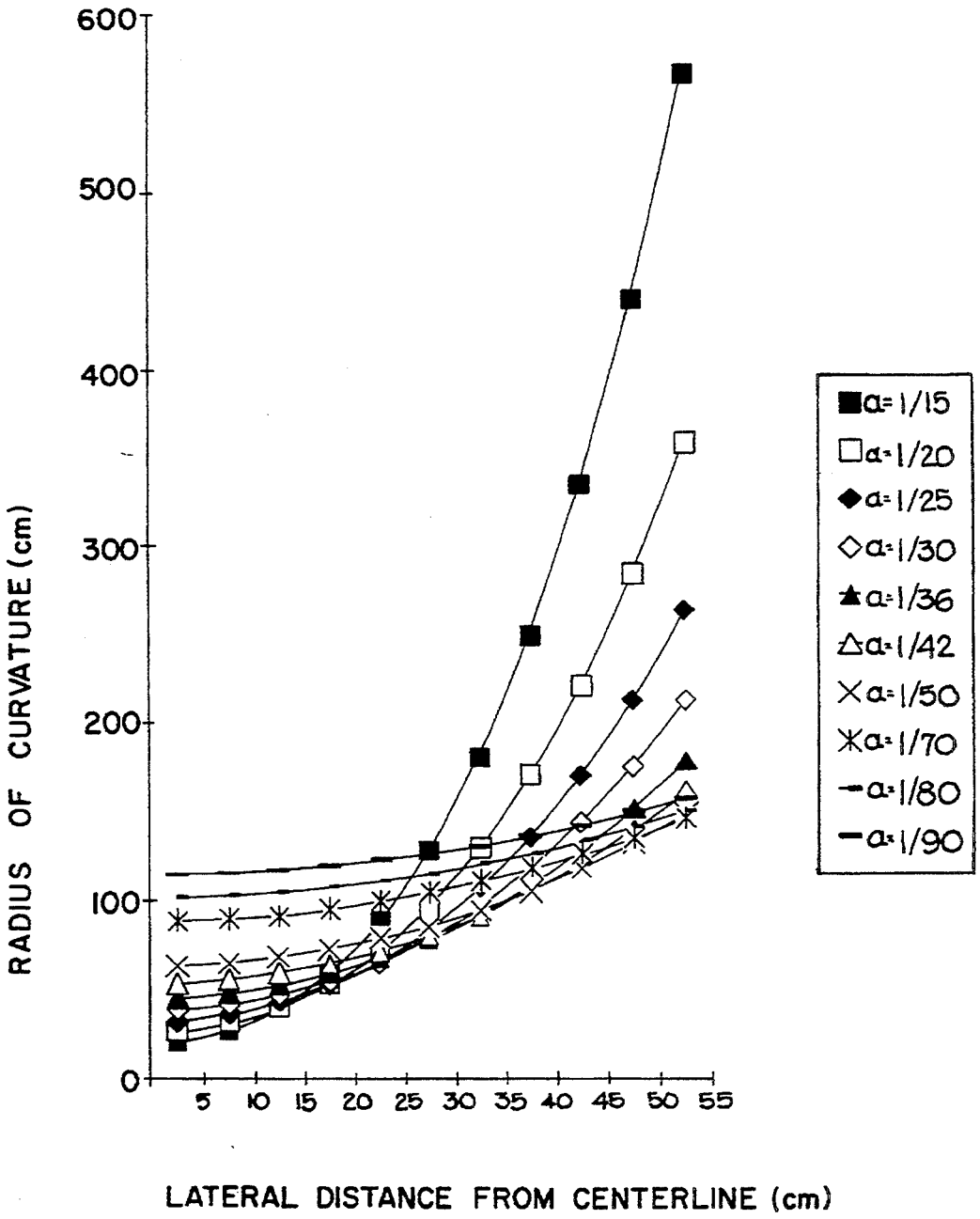
FIG. 2 is a graphical representation of the increase in radii of curvature of various belt halves of FIG. 1, as a function of lateral position from the centerline.

The data of Table I are graphically represented in FIG. 2 which shows the increase in radius of curvature (vertical axis) as a function of the lateral position (horizontal axis) of the edge 16. As illustrated by FIG. 2, belts 12 which have a constant a with a value less than about 1/70 exhibit too little change in radius of curvature and behave similar to a generally rectangularly shaped straight belt 12. Conversely, belts 12 which have a constant a with a value greater than about 1/25 have distal ends 42 which generally are disposed too far above the waistline of the wearer.

A less preferred manner in which the radius of curvature may increase as distal end 42 of the belt 12 is approached is to have edges 16 of nonconcentric and unequal radii of curvature. If nonconcentric and unequal radii of curvature are selected for the belt 12, the centric and equal radii of curvature is approximated.

Referring to FIG. 3, to apply the garment 10 to the wearer, a clean and sanitary disposable assembly 14 is provided and may be attached to either face of the belt 12, using the indicia 44, or positions intermediate the indicia 44, as desired. To facilitate such attachment, the flaps 30 may be inflected at the rear waist margin 34, so that the pair of patches 18 of hook type material at the rear waist margin 34 face opposite the pair of patches 18 at the front waist margin 32. The pair of rear waist margin 34 patches 18 are then attached to a first face of the belt 12. The wearer sits or stands, holding one end of the belt 12 in each hand with the disposable assembly 14 behind the wearer and downwardly oriented. The wearer encircles his or her waist with the belt 12, and secures the ends of the belt 12 to any intermediate segment 52 of the belt 12 having receiving material by using the fastening means on each end of the belt 12.

The disposable assembly 14 is then brought between the legs of the wearer and secured in front of the wearer to the opposite or second face of the belt 12 using the remaining pair of hook type patches 18 at the front waist margin 32. Utilizing this arrangement, the pair of hook type patches 18 at the rear waist margin 34 of the disposable assembly 14 is attached to the face of the belt 12 which is inwardly oriented (towards the waist of the wearer) and the pair of hook type patches 18 at the front waist margin 32 is attached to the outwardly oriented face of the belt 12 (away from the wearer).

By attaching the front waist margin 32 of the disposable assembly 14 to the exterior face of the belt 12, the garment 10 is easily inspected for soiling. If soiled, the disposable assembly 14 is detached from the belt 12 and replaced with a new disposable assembly 14. The belt 12 is reused, and laundered as necessary.

Figure 4:
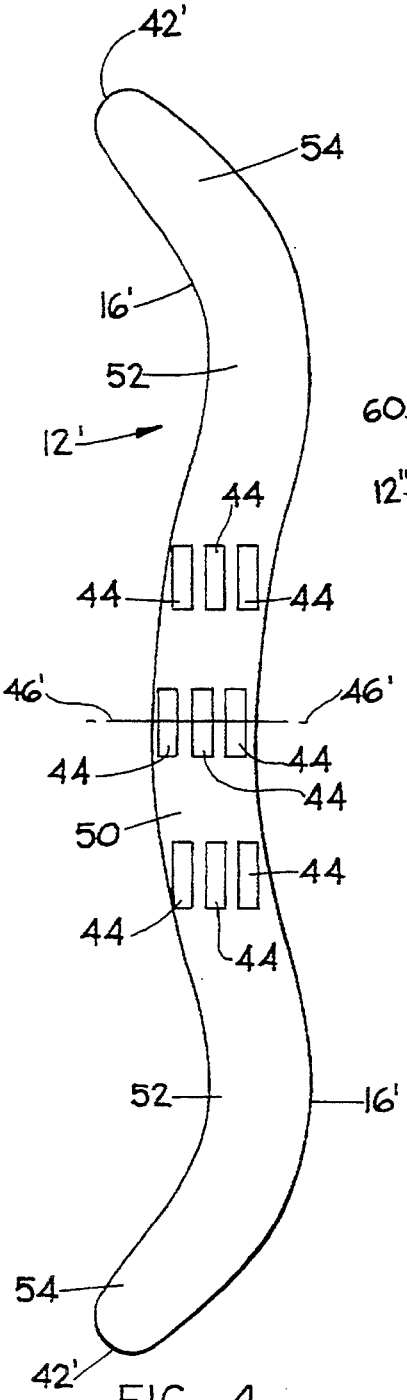
FIG. 4 is a top plan view of a second embodiment of a belt according to the present invention.

Referring to FIG. 4, a second embodiment of a belt 12' according to the present invention is shown. Under dynamic conditions this belt 12' is adapted to not impact the portions of the wearer's body having relatively large degrees of motion and has a different means for causing one laterally extending edge 16' to have a length greater than that of the other laterally extending edge 16' whereby the belt conforms to the shape of the wearer, particularly five independent and juxtaposed segments: a central segment 50, two intermediate segments 52 and two distal segments 54. The width of the belt 12' of this embodiment should be less than about 12 centimeters, and is preferably about 6 to about 8 centimeters. If a wider belt 12' is selected for this embodiment, the belt 12' may not rest, as desired, on the tailbone or the uppermost laterally extending edge 16' of the belt 12' may chafe the back and sides of the wearer, leading to discomfort.

The belt 12' has a central segment 50 originating at, adjacent to, or juxtaposed with the centerline 46' of the belt 12'. The central segment 50 extends laterally outwardly from the centerline 46' in opposite directions, towards the oppositely disposed distal ends 42' of the belt 12'. The central segment 50 has an inboard origin at the longitudinal centerline 46' and terminates at two outboard ends, each generally symmetrically and oppositely disposed from the centerline 46'. The outboard end is the part of the central segment 50 closest to the respective distal ends 42' of the belt 12' and furthest from the centerline 46'.

The laterally extending edges 16' of the central segment 50 are coplanarly arcuate within the plane of the belt 12' and concave in a first direction. When the belt 12' is worn in its desired orientation, the first direction is concave downward.

Each laterally extending edge 16' of the central segment 50 should outwardly extend about 16 to about 23 centimeters from the centerline 46' as measured along the laterally extending edge 16' or about 12 to about 18 centimeters as rectilinearly measured in the lateral direction.

The laterally extending edges 16' of the central segment 50 are preferably nonconcentric and have equal radii of curvature. The radii of curvature at the longitudinal centerline 46' may be about 35 centimeters, more preferably are infinite, and even more preferably are about 114 centimeters. At the outboard ends of the central segment 50, the radii of curvature of both laterally extending edges 16' may increase to about 50 centimeters, more preferably to an infinite radius of curvature, and even more preferably to about 120 centimeters.

Juxtaposed or adjacent each outboard end of the central segment 50 is an intermediate segment 52. Each intermediate segment 52 is disposed outboard of the distal end 42' of the central segment 50 and has an inboard end adjacent to or juxtaposed with the outboard end of the central segment 50. Each intermediate segment 52 further has an outboard end longitudinally oppositely disposed from the inboard end in a sense oriented towards the distal end 42' of the belt Each intermediate segment 52 has two laterally extending edges 16' arcuate with the plane of the belt 12' and concave in a second direction, the second direction of concavity is generally opposite that of the first direction of concavity. When the belt 12' is encircled about a standing wearer each intermediate segment 52 is generally concave upwards.

The intermediate segment 52 lateral edges 16' may have nonconcentric and equal radii of curvature. The intermediate segment 52 may be generally circular and should have a radius of curvature of about 23 to about 33 centimeters between the laterally extending edges 16, and may even be straight. Each intermediate segment 52 should be about 13 to about 20 centimeters in length, as measured along the laterally extending edge 16'. If the laterally extending edges 16' of the intermediate segments 52 are greater in length, the belt 12' may interfere with the genitalia of the wearer. If the laterally extending edges 16' of the intermediate segments 52 are shorter in length, the belt 12' may interfere with the stomach bulge of the wearer.

Outboard of each intermediate segment 52 and forming the inboard boundary of each distal end 42' are the distal segments 54 of the belt 12'. The belt 12' has two distal segments 54, one on each side of the centerline 46'. The distal segments 54 are a generally rectilinear projection of the tangent of the outboard end of the respective intermediate segment 52. The distal segment 54 should be long enough so that each distal end 42' may be overlapped with the opposite distal segment 54. An distal segment 54 having a length along the laterally extending edge 16' of about 10 to about 26 centimeters is generally suitable.

Figure 5:
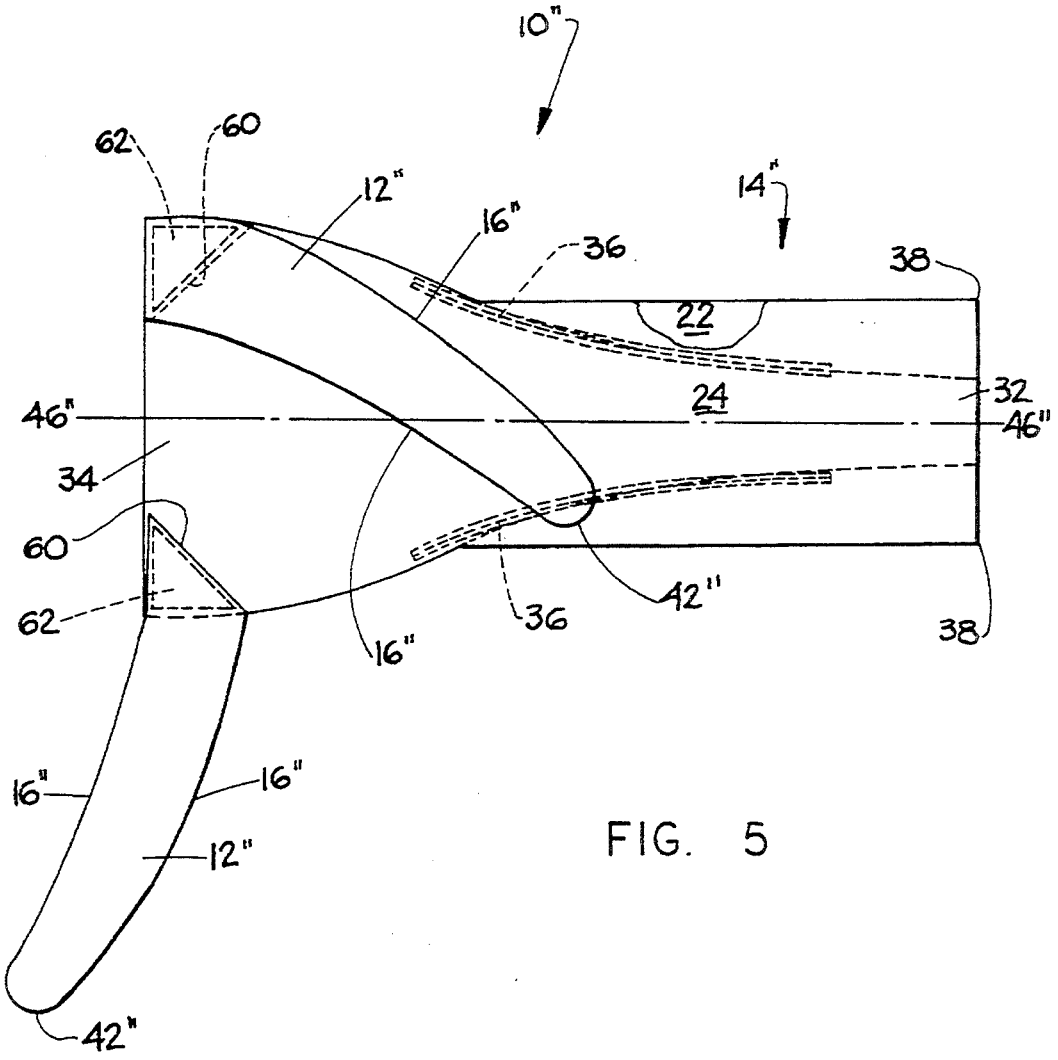
FIG. 5 is a bottom plan view of a second execution of a disposable absorbent garment having an integral belt of the embodiment shown in FIGS. 1 and 3, with one portion of the belt shown in the extended position and the distal end of one portion of the belt affixed to the backsheet of the disposable absorbent garment.

Referring to FIG. 5, if it is desired, the belt 12'' and disposable assembly 14'' may be joined and not detachable. In one execution, an embodiment of a belt 12'' according to the present invention may have a proximal end 60 joined to the outwardly oriented face of the backsheet 24 with a patch of adhesive 62. The distal ends 42'' of this belt 12'' may either be free or, preferably, are removably attached to the backsheet 24. The proximal ends 60 need not laterally coincide, and are preferably longitudinally aligned and laterally spaced apart.

A particularly preferred patch of adhesive 62 monotonically increases in width as the rear waist margin 34 is approximated, to provide for better distribution of the stresses associated with encircling the belt 12'' about the waist of the wearer. To accomplish the desired stress distribution, the proximal end 60 of the belt 12'' may be adhesively joined to the outwardly oriented face or the backsheet 24, preferably using a generally triangularly shaped patch of adhesive 62. One particularly preferred patch 62 is shaped like a right triangle having one leg oriented parallel to the longitudinal axis, one leg oriented parallel to the lateral axis and a hypotenuse oriented at a diagonal relative to the waist margin of the disposable assembly 14″.

Figure 6:
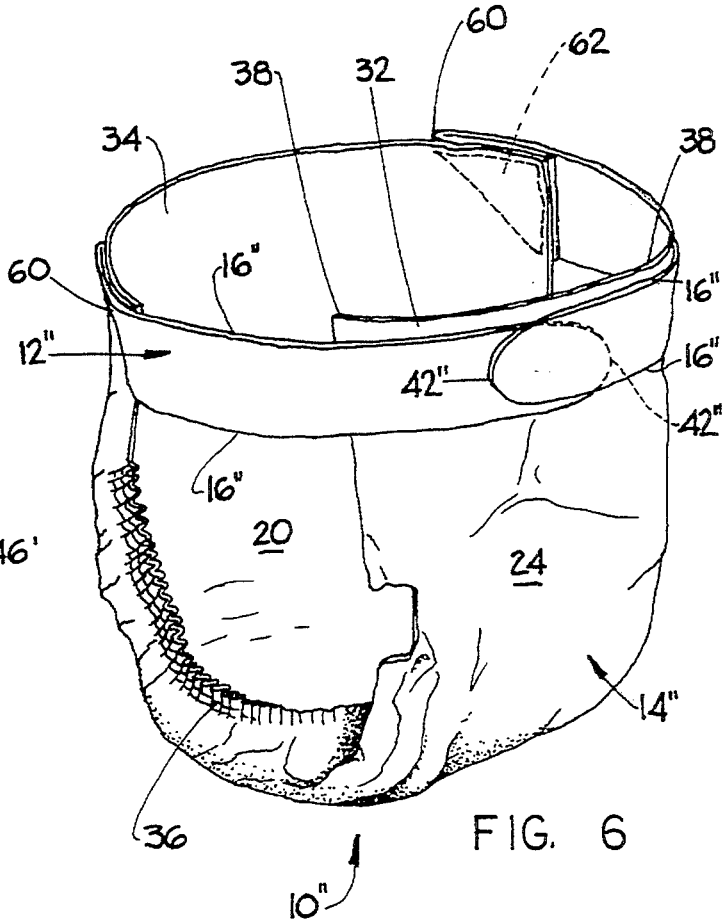
FIG. 6 is a perspective view of the absorbent garment shown in FIG. 5.

As illustrated in FIG. 6, such a belt 12″ may be comprised of two halves, one half encircling the left side of the wearer and one half encircling the right side of the wearer. The belt 12″ may overlay the backsheet 24 for ease of manufacturing, packaging and handling until ready for use. The distal end 42″ of the belt 12″ may be detachably associated with the backsheet 24 until the garment 10 is to be worn.

With continuing reference to FIG. 6, when it is desired to place the garment on a wearer, the distal end 42 of the belt 12″ is detached from the backsheet 24 and brought about the waist of the wearer as described above. Either of the two aforementioned embodiments of belts 12″, or the following embodiment, may be used with this execution. However, the illustrated embodiment of FIGS. 1 and 3 provides the advantage that the belt 12″ is conveniently circumscribed by the marginal areas of the disposable assembly 14″ while the distal end 42″ of the belt 12″ remains attached to the outwardly oriented face of the backsheet 24.

While the execution of FIGS. 5–6 is illustrated with the belt 12″ embodied by FIGS. 1–3, it is to be understood this execution could equally readily utilize any other embodiment of a belt 12″, such as but not limited to the other two described herein, and still fall within the scope of the claimed invention.

Figure 7:
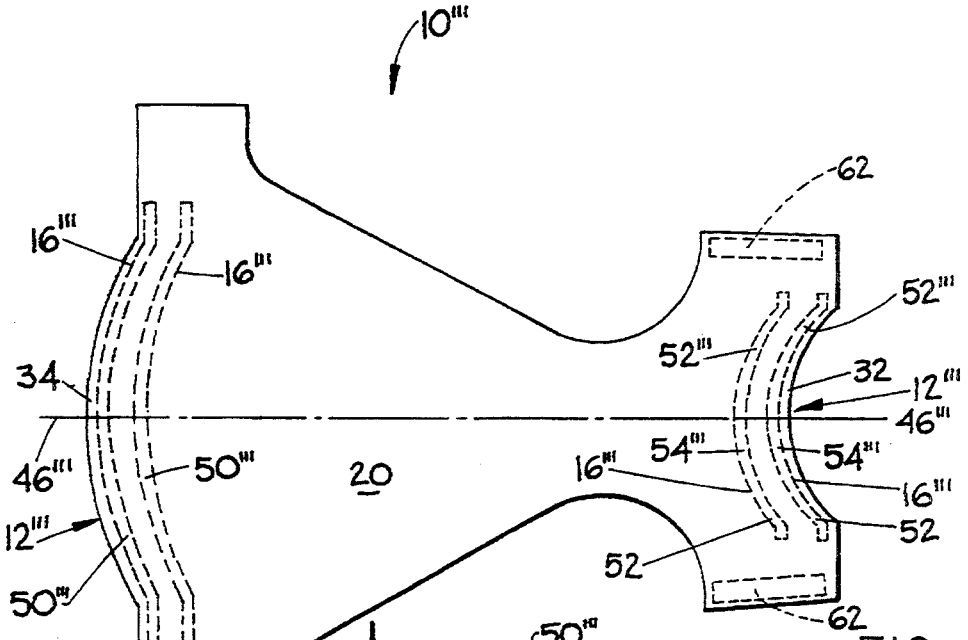
FIG. 7 is a top plan view of a third execution of a disposable absorbent garment having an integral belt of the embodiment shown in FIG. 4 and a disposable assembly with no distinct boundaries or separation from the belt.

Referring to FIG. 7, it may be desired that the belt 12‴ embodied by FIG. 4 and the disposable assembly 14‴ be unitary, integral and not have distinct or coterminous boundaries. In such an execution the belt 12‴ is typically not reusable. One laterally extending edge 16‴ of such belt 12‴ is disposed at the waist margin 32 or 34 of the disposable absorbent garment 10‴ and the other laterally extending edge 16‴ is by definition at, or juxtaposed with, the transverse edge of the core 22, so that the belt 12‴ comprises the region intermediate the core 22 and the outer edge of the waist margins 32 or 34 of the disposable absorbent garment 10‴.

Such an execution is closely related to disposable diapers as are currently well known in the art. A particularly preferred disposable diaper is described in U.S. Pat. 3,860,003, issued Jan. 3, 1979 to Buell, which patent is incorporated herein by reference for the purpose of showing a particularly preferred construction of a disposable absorbent garment 10‴ having an integral belt 12‴ and disposable assembly 14‴ according to the present invention. In such an arrangement the rear waist margin 34 of the disposable absorbent garment 10‴ is convex inward in the flat position of FIG. 7. The front waist margin 32 is convex outward in the flat position of FIG. 7.

The belt 12‴ comprises elastic such as a single or substantially parallel multiple elastic strands, or other restraining means, so that the laterally extending edges 16‴ of the rear waist margin 34 have convex downward first coplanar concavity of the central segment 50‴ described above relative to the second embodiment for the standing wearer. The waist margins 32 and 34 further define intermediate segments 52‴ which, when the garment is worn, are oriented diagonally downwardly across the hips towards the front of the wearer. The distal segments 54‴ are adjacent or juxtaposed with the intermediate segments 52‴ and are circumferentially disposed at the front waist margin 32.

Figure 8:
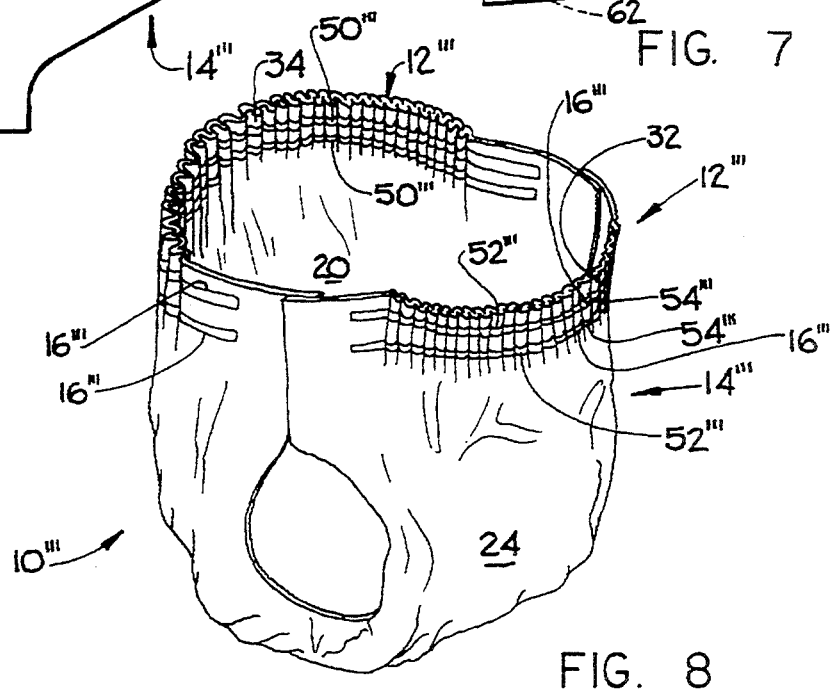
FIG. 8 is a perspective view of the absorbent garment execution shown in FIG. 7.

As illustrated in FIG. 8, utilizing such an arrangement the elastic of the rear waist margin 34 is preferentially perched on or otherwise supported by the tailbone of the standing wearer. This prevents the frame which holds the diaper in place on the wearer from interfering with the backside of the wearer's body during normally encountered movements.

Similarly, the concave upward geometry of the front of the disposable absorbent garment 10‴ is preferentially disposed below the stomach and abdomen of the wearer and above the genitalia, so that if the stomach of the wearer projects or protrudes forward, the stomach will not rub, abrade or otherwise press outwardly against the front portion of the disposable absorbent garment 10‴. In a particularly preferred execution, the stomach will overhang the laterally extending edge 16‴ of the front waist margin 32 so that hoop stresses against the disposable absorbent garment 10‴ are minimized.

It will be apparent to one skilled in the art that the execution of FIGS. 7–8 is not limited to the belt 12 embodiment of FIG. 4, but may be utilized, for example, with the embodiment of FIGS. 1–3, the following embodiment or with any other embodiment according to the claimed invention. It will be further apparent that the belt 12, or other retaining means, of the execution of FIGS. 7–8 need not fully circumscribe the wearer, but may have relatively small intermittent gaps, spaces or discontinuities and still perform its intended function and fall within the scope of the claimed invention.

Figure 9A:
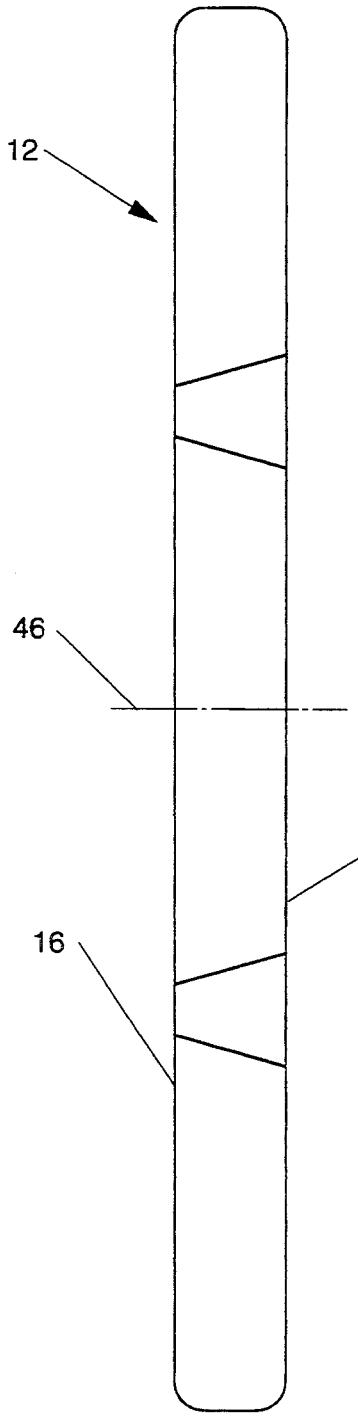
FIG. 9A is a top plan view of a third embodiment of a belt according to the present invention in which a generally straight and rectangular belt is provided with pieces of elastic material in the shape of truncated triangles.
Figure 9B:
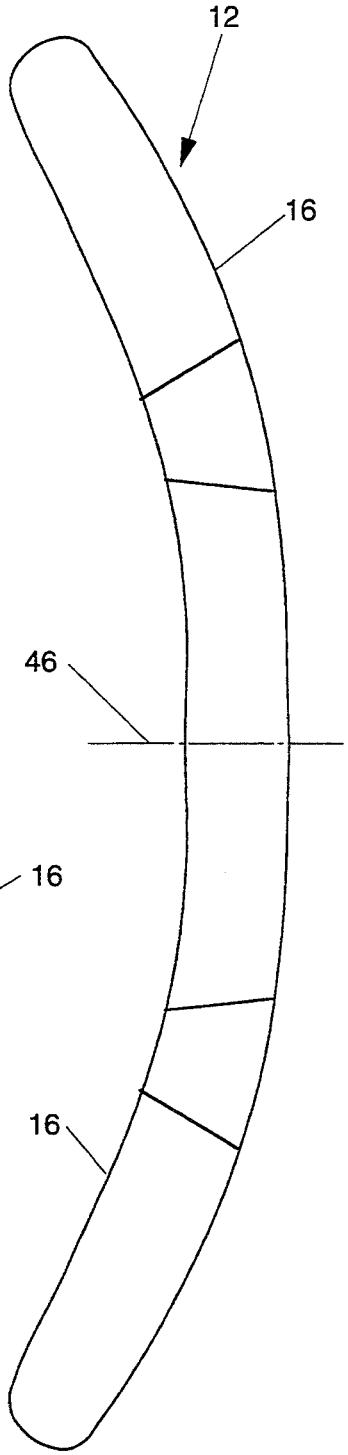
FIG. 9B is a top plan view of the belt shown in FIG. 9A which illustrates the manner in which the differential extensibility of the pieces of elastic provides the belt with one edge having a length greater than the other edge.

In a third embodiment shown in FIGS. 9A and 9B a belt suitable for use with any of the foregoing executions, particularly the executions of FIGS. 1–5, the means for causing one laterally extending edge 16 of the belt 12 to have a length greater than the other laterally extending edge 16 of the belt 12 whereby the belt 12 is fitted to the shape of the wearer is one or more pieces of elastic in the belt 12. Preferably the elastic extends throughout the entire width of the belt 12. The elastic should provide a differential extensibility, as measured in the lateral direction, across the width of the belt 12. As used herein the term "differential extensibility" refers to a difference in elongation, per unit applied force or a difference in maximum elongation, as applied and measured principally in the lateral direction of the patch of elastic. The differential extensibility may be achieved by having a variable spring rate throughout the width of the elastic or, preferably, by having different extensions before the maximum elongation is reached.

As shown in FIG. 9A, in a particularly preferred execution a patch of elastic is used between the two laterally extending edges 16 of the belt 12. The patch of elastic is tapered, so that it monotonically decreases in the longitudinal dimension as one laterally extending edge 16 of the belt 12, preferably the edge which is upwards when the belt 12 is worn, is approximated. Particularly preferred shapes for the patches of elastic include truncated triangles and parabolic shapes having the shorter lateral dimension towards the laterally extending edge 16 of the belt 12 which is of higher elevation when the garment 10 is worn by a standing wearer. Preferably, the elastic patch does not have a vertex, or other constraint preventing elongation.

As shown in FIG. 9A, in a particularly preferred execution two elastic patches, as described above, are incorporated into a straight and rectangularly shaped belt 12 according to the present invention. Each patch is isomerically and equally distributed from the centerline 46 of the belt 12. A particularly preferred elastic patch has a spring rate of about 50 grams per centimeter at about 20 percent elongation and extends about 210 percent before the maximum elongation of either laterally extending edge 16 is reached and extends to about 10–20 percent elongation in use. Each patch is preferably centered about 17 to about 23 centimeters from the centerline 46 of the belt 12. Particularly preferred elastic 36 is supplied by the Darlington Fabrics Corporation of New York, New York, and sold under the tradename Tecsheen Style 5676.

Elastic patches shaped like a truncated triangle and having a length of about 2 to 8 centimeters at one laterally extending edge 16, particularly the laterally extending edge 16 of higher elevation on a standing wearer, and about 5 to 13 centimeters at the other laterally extending edge 16, particularly the edge of lower elevation on a standing wearer, has been found to work well for a belt 12 having a width of about 10 centimeters. It will be apparent to one skilled in the art that the elastic patches may be used either with an arcuately shaped belt 12, such as that shown in the FIGS. 1 and 4 or, if desired, with a generally straight and rectangularly shaped belt 12, as shown in FIGS. 9A, and still fall within the spirit and scope of the claimed invention.

Figure 10:
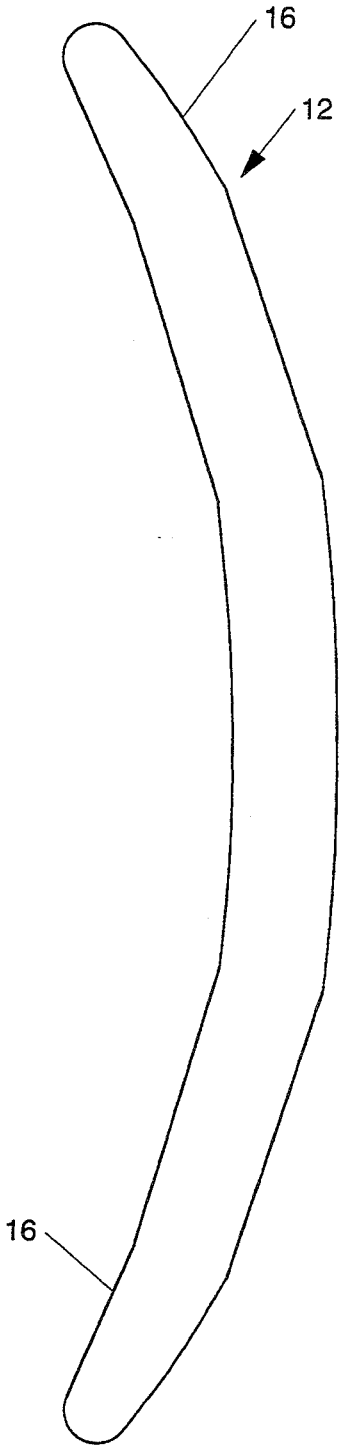
FIG. 10 is a top plan view of an embodiment of the belt of the present invention in which the edges of the belt are comprised of adjacent rectilinear and curvilinear segments.

It will be apparent to one skilled in the art that several other variations are feasible. For example as shown in FIG. 10 the arcuate edges of the belt 12 of FIGS. 1–3 need not be curvilinear, but may be comprised of and approximated by two ( or more ) adjacent or juxtaposed discrete rectilinear segments, or adjacent rectilinear and curvilinear segments. All such variations are within the spirit and scope of the claimed invention.

What is claimed is:

1. An absorbent garment to be fitted to a wearer having a front portion, a rear portion, and a longitudinal centerline, said front portion being concave upward when said absorbent garment is worn, said absorbent garment comprising:

a belt portion for encircling at least a portion of a wearer's waist, said belt portion having a centerline which corresponds in position to a wearer's spinal cord when the absorbent garment is worn, a first face and a second face opposed thereto, two spaced apart laterally extending edges generally centered about said centerline, wherein said laterally extending edges comprise an upper laterally extending edge and a lower laterally extending edge wherein the upper laterally extending edge is disposed above the lower edge when the absorbent garment is worn and the highest portion of the belt portion on the wearer's body at a rear of the wearer's body is in the area of the wearer's spinal cord at the inner section of the centerline of said belt portion and said upper laterally extending edge, and said belt portion curves downward toward a front of the wearer's body when the absorbent garment is worn; and a disposable assembly associated with said belt portion, said disposable assembly comprising a liquid pervious topsheet, a liquid impervious backsheet joined to said topsheet, an absorbent core positioned between said topsheet and said backsheet, and a means for affixing said disposable assembly to at least one face of said belt portion.

2. A garment according to claim 1 wherein said belt portion has at least one proximal end joined to said backsheet.

3. A garment according to claim 1 wherein said belt portion comprises three discrete segments:

a central segment having laterally extending edges originating at or juxtaposed with the centerline and extending laterally outwardly therefrom in each direction towards the oppositely disposed distal ends, said laterally extending edges of said central segment being arcuate within the plane of said belt portion and concave in a first direction;

two intermediate segments disposed outboard of said central segment, one said intermediate segment being on each side of the centerline, each of said intermediate segments having an inboard end adjacent to or juxtaposed with said central segment and an outboard end disposed laterally oppositely therefrom, each of said laterally extending edges of said intermediate segments being arcuate within the plane of said belt portion and concave in a second direction generally opposite that of said first direction of said central segment; and two distal segments, one said distal segment on each side of the centerline, each said distal segment being between said respective intermediate segment and the respective distal end, each said distal segment being a generally rectilinear projection of the tangent of the outboard end of said respective intermediate segment.

4. A garment according to claim 1 wherein the means for affixing said disposable assembly to at least one face of said belt portion comprises an association between the disposable assembly and the belt such that the relationship between the disposable assembly and the belt are selected from the group consisting of integral, joined at a proximal end, and detachable.

5. A garment according to claim 4 wherein said belt portion is integral and comprises elastic strands.

6. A garment according to claim 1 wherein said belt portion comprises at least one elastic segment having differential extensibility, as measured in the lateral direction, across the finite width of said belt portion.

7. A belt according to claim 6 wherein said elastic segments monotonically decrease in lateral dimension as one laterally extending edge of the belt portion is approached.

8. A garment according to claim 1 wherein a portion of each said laterally extending edge is arcuate within the plane of the belt portion concave in the same direction.

9. A belt according to claim 8 wherein said arcuate portion has a curvilinear segment which increases in radius of curvature as a distal end of said belt portion is approached.

10. A disposable absorbent article having a front end edge and a rear end edge, said disposable absorbent article comprising a liquid pervious topsheet, a liquid impervious backsheet joined to said topsheet, and an absorbent core positioned between said topsheet and said backsheet, wherein said front end edge of said disposable absorbent article is concave upward and disposed below a wearer's stomach and abdomen when said disposable absorbent article is worn.

11. The disposable absorbent article of claim 10 further comprising at least one elastic strand adjacent said front end edge of said absorbent article.

12. The disposable absorbent article of claim 10 wherein said rear end edge comprises a convex upward waistband portion for encircling at least a portion of a wearer's waist when said disposable absorbent article is worn.

13. The disposable absorbent article of claim 12 further comprising at least one elastic strand adjacent said rear end edge of said absorbent article.

* * * * *